United States Patent [19]
Zare et al.

[11] Patent Number: 5,815,277
[45] Date of Patent: Sep. 29, 1998

[54] DEFLECTING LIGHT INTO RESONANT CAVITIES FOR SPECTROSCOPY

[75] Inventors: Richard N. Zare, Stanford, Calif.; Juergen Martin, Harxheim, Germany; Barbara A. Paldus, Stanford, Calif.

[73] Assignee: The Board of Trustees of the Leland Stanford Junior Univesity, Stanford, Calif.

[21] Appl. No.: 949,242

[22] Filed: Oct. 10, 1997

Related U.S. Application Data

[63] Continuation-in-part of Ser. No. 879,975, Jun. 20, 1997.
[51] Int. Cl.$^6$ ..................................................... G01N 21/17
[52] U.S. Cl. ........................................ 356/440; 356/440
[58] Field of Search .................................. 356/432, 437, 356/439, 400; 250/243

[56] References Cited

U.S. PATENT DOCUMENTS 3,995,231  11/1976  Johnson et al. .......................... 372/18
5,528,040   6/1996  Lehmann .................................. 250/343

OTHER PUBLICATIONS

Romanini et al., "CW cavity ring down spectroscopy" *Chemical Physics Letters* 264 (1997) 316, 322, 10 Jan. 1997.

*Primary Examiner*—Richard A. Rosenberger
*Attorney, Agent, or Firm*—Lumen Intellectual Property Services

[57] ABSTRACT

Light is coupled into a cavity ring down spectroscopy (CRDS) resonant cavity using an acousto-optic modulator. The AOM allows in-coupling efficiencies in excess of 40%, which is two to three orders of magnitude higher than in conventional systems using a cavity mirror for in-coupling. The AOM shutoff time is shorter than the roundtrip time of the cavity. The higher light intensities lead to a reduction in shot noise, and allow the use of relatively insensitive but fast-responding detectors such as photovoltaic detectors. Other deflection devices such as electro-optic modulators or elements used in conventional Q-switching may be used instead of the AOM. The method is particularly useful in the mid-infrared, far-infrared, and ultraviolet wavelength ranges, for which moderately reflecting input mirrors are not widely available.

24 Claims, 3 Drawing Sheets

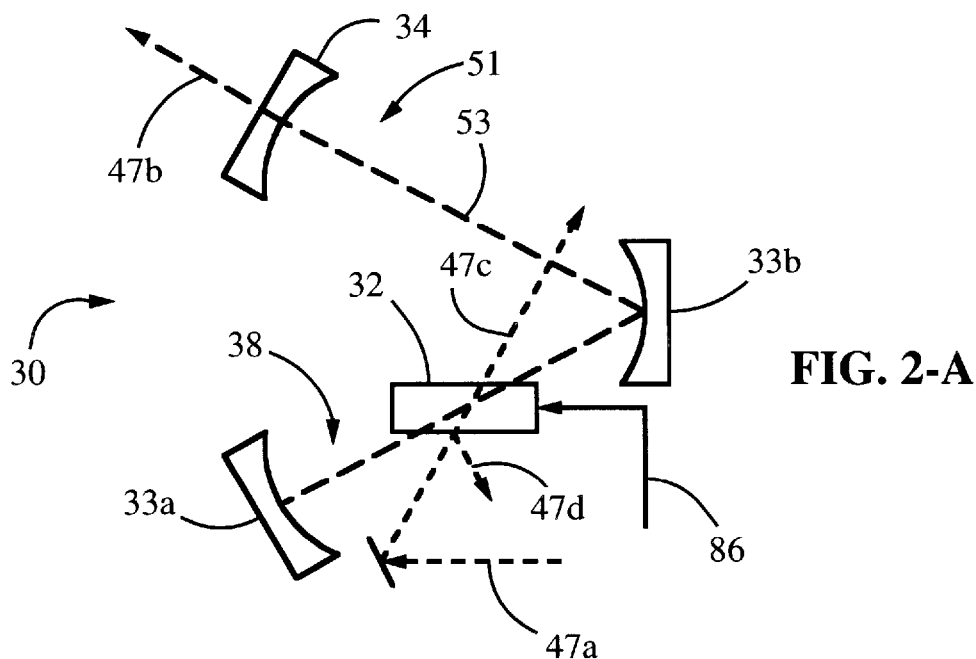
FIG. 2-A
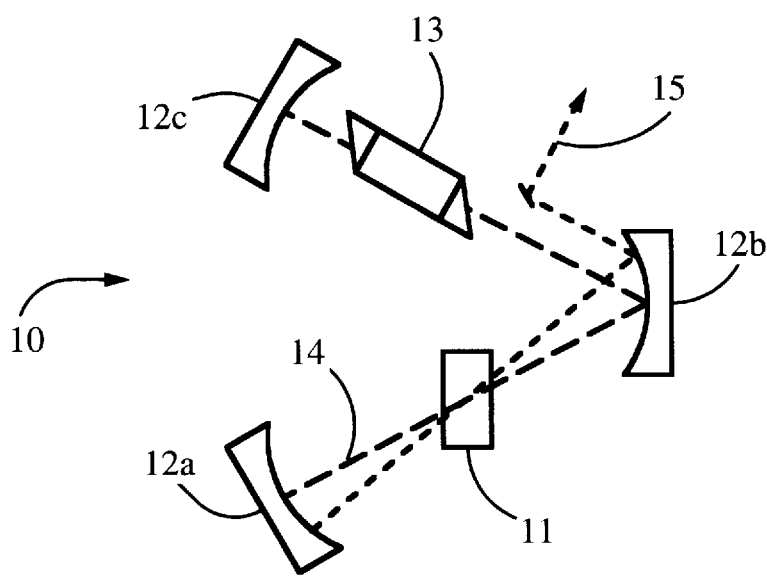
FIG. 2-B
PRIOR ART

DEFLECTING LIGHT INTO RESONANT CAVITIES FOR SPECTROSCOPY

RELATED APPLICATION DATA

This application is a continuation-in-part of U.S. patent application Ser. No. 08/879,975, filed Jun. 20, 1997, and is related to co-pending U.S. patent application "Spectroscopy Using Active Diode Laser Stabilization by Optical Feedback," by inventors Richard N. Zare, Juergen Martin, and Barbara A. Paldus. The above-referenced applications are assigned to the assignee of the present invention, and are herein incorporated by reference.

U.S. GOVERNMENT RIGHTS

This invention was made with U.S. Government support under grant No. DE-FG03-92ER14304, awarded by the Department of Energy. The U.S. Government has certain rights in this invention.

FIELD OF THE INVENTION

This invention relates to the field of spectroscopy, and in particular to deflecting light into spectroscopic resonant cavities for increasing intracavity light intensity.

BACKGROUND OF THE INVENTION

Traditional spectroscopic methods are limited in sensitivity to approximately one part per ten thousand ($1:10^4$) to one part per hundred thousand ($1:10^5$). The sensitivity limitation arises from instabilities in light source intensity that are translated into noise in the absorption signal. For general information on traditional spectroscopy methods see for example Dereniak and Crowe, *Optical Radiation Detectors*, John Wiley & Sons, New York, 1984, and Demtroder, *Laser Spectroscopy*, Springer, Berlin, 1996.

Cavity Ring-Down Spectroscopy (CRDS), a technique first described by O'Keefe and Deacon in an article in *Rev. Sci. Instrum.* 59(12):2544–2551 (1988), allows making absorption measurements with sensitivities on the order of one part per ten million ($1:10^7$) to one part per billion ($1:10^9$) or higher. For general information on CRDS see U.S. Pat. No. 5,528,040 by Lehmann, herein incorporated by reference, as well as the articles by Romanini and Lehmann in *J. Chem. Phys.* 102(2):633–642 (1995), Meijer et al. in *Chem. Phys. Lett.* 217(1–2):112–116 (1994), Zalicki et al. in *App. Phys. Lett.* 67(1):144–146 (1995), Jongma et al. in *Rev. Sci. Instrum.* 66(4):2821–2828 (1995), and Zalicki and Zare in *J. Chem. Phys.* 102(7):2708–2717 (1995).

In a conventional CRDS system, the sample (absorbing material) is placed in a high-finesse stable optical resonator consisting of two spherical mirrors facing each other along a common optical axis. Light incident on one mirror circulates back and forth multiple times in the resonator, setting up standing waves having periodic spatial variations. Light exiting through the other mirror measures the intracavity light intensity.

The radiant energy stored in the resonator decreases in time (rings-down). For an empty cavity, the stored energy follows an exponential decay characterized by a ring-down rate that depends only on the reflectivity of the mirrors, the separation between the mirrors, and the speed of light in the cavity. If a sample is placed in the resonator, the ring-down is accelerated; under suitable conditions, the intracavity energy decays almost perfectly exponentially. An absorption spectrum for the sample is obtained by plotting the reciprocal of the ring-down rate versus the wavelength of the incident light.

CRDS has been applied to numerous systems in the visible, ultraviolet, and infrared. For information on the use of CRDS for spectroscopy in the visible, see the articles by Engeln and Meijer in *Rev. Sci. Instrum.* 67(8): 2708–2713 (1996), Martin et al. in *Chem. Phys. Lett.* 258(1–2):63–70 (1996), Paul et al. in *J. Chem. Phys.* 104(8):2782–2788 (1996), Scherer et al. in *J. Chem. Phys.* 103(21):9187–9192 (1995), Scherer et al. in *J. Chem. Phys.* 102(13):5190–5199 (1995), Scherer et al. in *Chem. Phys. Lett.* 242(4–5):395–400 (1995). Heustis et al. in *Canadian J. Phys.* 72(11–12):1109–1121 (1994), and O'Keefe et al. in *Chem. Phys. Lett.* 172(3–4):214–218 (1990). Information on CRDS applications in the ultraviolet can be found in the above-referenced articles by Romanini and Lehmann, and Zalicki et al., as well as the articles by Zhu et al. in *Chem. Phys. Lett.* 257(5–6):487–491 (1996), Romanini and Lehmann in *J. Chem. Phys.* 105(1):81–88 (1996), Romanini and Lehmann in *J. Chem. Phys.* 105(1):68–80 (1996), Wahl et al. in *Diamond and Related Materials* 5(3–5):373–377 (1996), Boogaarts and Meijer in *J. Chem. Phys.* 103(13):5269–5274 (1995), Zalicki et al. in *Chem. Phys. Lett.* 234(4–6), 269–274 (1995), Jongma et al. in *J. Molecular Spectroscopy* 165(2):303–314 (1994), and Romanini and Lehmann in *J. Chem. Phys.* 99(9):6283–6301 (1993). For information on the use of CRDS for infrared spectroscopy see the above-referenced article by Martin et al., as well as the article by Scherer et al. in *Chem. Phys. Lett.* 245(2–3):273–280 (1995).

In comparison to conventional spectroscopy techniques, CRDS is advantageous because of the increased pathlength due to multiple reflections. CRDS is also advantageous because of its relative insensitivity to variations in the amplitude of light generated by the light source. In a CRDS system, fluctuations in the intensity of the light source do not typically limit sensitivity.

CRDS sensitivity can be limited by undesirable optical feedback the laser used for illumination. For more information on the optical feedback problem see the above-incorporated co-pending applications. The sensitivity of CRDS systems may also be limited by shot noise. Shot noise is of particular concern in wavelength ranges for which it is difficult to obtain mirrors that have good transmission properties. Such wavelength ranges include the mid- and far-infrared, and the ultraviolet. In such ranges, available mirrors that are not perfectly reflective have poor transmission properties and high scattering losses (T+R+S=1, where T, R, S are transmission, reflection, and scattering coefficients, respectively); the input and output mirrors then introduce relatively large optical losses in the system.

Shot noise may limit not only the wavelength ranges in which adequate CRDS measurements can be performed, but also the types of detectors that can be used. In the absence of strong output signals, detector types that have high temporal response but low sensitivity (e.g. photovoltaic detectors such as photodiodes) may not be suitable for use in conventional CRDS system. Shot noise is of concern for many non-CRDS applications. A method of increasing the amplitudes of output signals from spectroscopic resonant cavities would find use in many non-CRDS applications.

OBJECTS AND ADVANTAGES OF THE INVENTION

In light of the above, it is a primary object of the present invention to provide a spectrometer comprising an intracavity input deflection means such as an acousto-optic modulator for deflecting light generated by a light source into a resonant cavity comprising a sample, without deflecting light resonating within the cavity. The use of a deflection means for coupling light into the cavity allows coupling efficiencies (and consequently, intracavity intensities) two to three orders of magnitude higher than in systems using an input mirror for in-coupling. The higher intracavity intensity leads to improved signal to noise ratio and reduced shot noise, and allows the use of photovoltaic detectors and alternative signal processing methods. The higher intracavity intensity also allows performing measurements in wavelength ranges including the mid- and far-infrared, for which moderately-reflective mirrors are not readily available. The use of a deflection means eliminates undesirable optical feedback from the cavity input back into the light source.

SUMMARY OF THE INVENTION

A system of the present invention comprises a light source, a resonant cavity in optical communication with the light source, an input deflection means situated within an intracavity light path defined by the resonant cavity, and an optical detector in optical communication with an output of the resonant cavity. The input deflection means deflects light generated by the light source onto the intracavity light path (along the optical axis of the cavity), while allowing light traveling along the intracavity light path to pass substantially undeflected. The detector detects light of a wavelength of interest extending from the cavity input, thus measuring an interaction of the sample with intracavity light of the wavelength of interest.

The light source preferably comprises a tunable, pulsed, far-infrared semiconductor laser. Alternatively, non-monochromatic, continuous-wave (c.w.) light sources generating light of a wide variety of wavelengths can be used. The input deflection means preferably comprises an acousto-optic modulator (AOM) cut at a Brewster's angle to the intracavity light path. Alternatively, the input deflection means may comprise an electro-optic modulator, a rotating mirror, a saturable absorber, or a thin-film absorber, among others. The detector is preferably a photovoltaic detector such as a photodiode; many other detectors types (e.g. photomultiplier tubes) are also suitable for use in a system of the present invention.

A wavelength tuning means tunes the wavelength of light incident on the detector within a range, for generating an absorption spectrum for that range. The wavelength tuning means is preferably part of the light source, but generally may be anywhere in the system before the detector. An optical isolator is situated between the input deflection means and the laser, for reducing an optical feedback to the laser due to back-reflections from various components. The light source and the input deflection means are situated relative to each other such that light extending from the input deflection means is not directed toward the light source. In particular, the light generated by the light source is not normal to the input deflection means, such that light reflected by the input deflection means is not directed toward the light source. The resulting reduction in optical feedback to the light source is particularly desirable for light sources comprising diode lasers, which generally are extremely sensitive to optical feedback.

A data analysis means is in electrical communication with the detector. The data analysis means receives from the detector signals characterizing the intensity of intracavity light (implicitly characterizing the interaction of the sample with intracavity light), and determines values of parameters of interest from the signals. Suitable parameters of interest include parameters characterizing the time-dependence of the intracavity light intensity, such as exponential (ring-up or ring-down) rates. Such exponential rates are indicative of the absorption of the sample at the corresponding wavelengths.

While continuous-wave light sources are suitable for use in a method of the present invention, pulsed light sources are preferred. A pulse generated by a pulsed light source is deflected onto the intracavity light path while the input deflection means is on. The input deflection means is turned off within an intracavity roundtrip time, such that the pulse traveling along the intracavity light path and incident on the input deflection means passes through substantially undeflected.

DESCRIPTION OF THE FIGURES

FIG. 2-A shows a prior art lasing cavity comprising an intracavity output deflector for dumping light out of the cavity.

FIG. 2-B shows a resonant cavity comprising an intracavity input deflector for coupling light into the cavity, according to the present invention.

DETAILED DESCRIPTION

Figure 1:
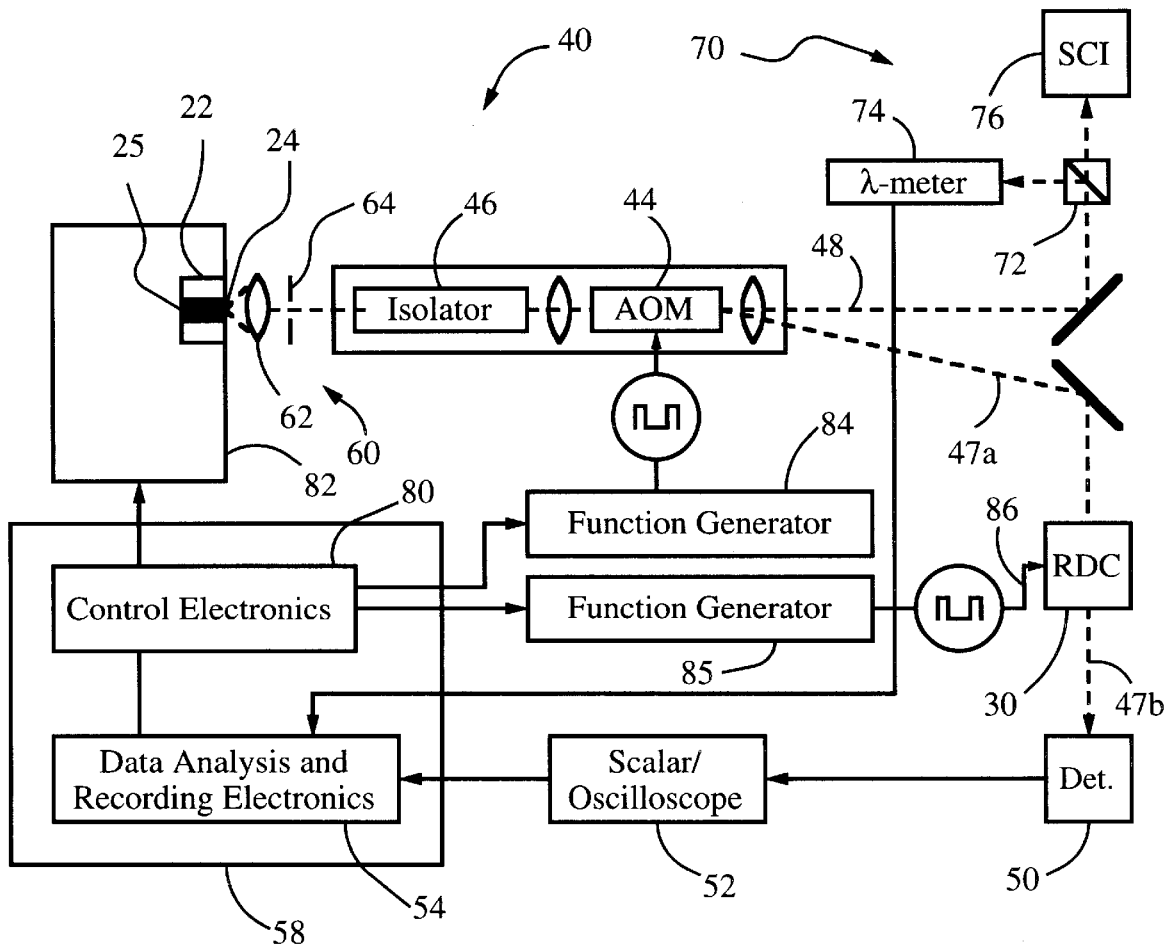
FIG. 1 is a high-level diagram of a system of the present invention.

FIG. 1 is a schematic diagram of a system 20 of the present invention. In FIG. 1, light beams are illustrated by dashed lines, while electrical connections are illustrated by solid lines. For clarity of presentation, various standard elements such as lenses and mirrors used for focusing and directing beams are not described; such elements are well known in the art.

System 20 comprises a light source 40 in optical communication with an input of a sample-holding resonant cavity 30. Light source 40 is capable of emitting light within a wavelength region of interest, commonly a wavelength region in which a sample has absorption features. Suitable wavelength regions of interest include the infrared and the visible. Generally, light source 40 can be a monochromatic or wide-spectrum source, as long as system 20 comprises some wavelength tuning means for controlling the wavelength of light detected by system 20. The wavelength tuning means may be part of light source 40 or may be situated within or after resonant cavity 30.

Preferably, light source 40 comprises a laser 22 having a laser output 24, and various pre-cavity optics including focusing and collimation optical components 60, an optical isolator 46, and an acousto-optic modulator (AOM) 44. Laser 22 is preferably a continuous wave (c.w.), tunable, infrared diode laser. Visible and ultraviolet lasers are also suitable. Depending on the application laser 22 can also be a pulsed dye or solid state (e.g. Ti:sapphire) laser. In general, light source 40 can also comprise a light emitting diode (LED), or a laser coupled to an optical parametric oscillator (OPO).

Optical components 60 comprise a laser collimation lens 62 for focusing the divergent light beam emerging through laser output 24, and a pinhole 64 for isolating laser 22 from back-reflections not along the optical axis of system 20. AOM 44 generates a first order beam 47a incident on cavity 30, and a zeroth order diagnostic beam 48 incident on diagnostic components 70. AOM 44 serves as a switch controlling the direction (and consequently the amplitude incident on cavity 30) of beam 47a. AOM 44 can be used to generate pulses or step inputs, among others. Isolator 46 isolates laser 22 from back reflections from AOM 44. AOM 44 and isolator 46 may also serve to stabilize diode laser 22 by providing frequency-shifted feedback of a suitable intensity to laser 22, as described in detail in the above-incorporated co-pending application "Spectroscopy Using Active Diode Laser Stabilization by Optical Feedback."

Laser 22 is controlled by a conventional laser controller 82 which includes current and temperature stabilization components. Control electronics 80 are electrically connected to controller 82, and to function generators 84, 85. In an embodiment suited for research applications, the functions of control electronics 80 are performed by a personal computer 58. In embodiments suited for industrial applications, all electronic and optical components are preferably integrated in a compact system.

A detector 50 is in optical communication with an output of cavity 30. Detector 50 detects an output beam 47b extending from cavity output 34, thus measuring the interaction of the intracavity sample with intracavity light of a spectrum of frequencies. Preferably, detector 50 is a photovoltaic detector such as a photodiode. Photodiodes are particularly suited for near-infrared detection. Other detector types may be better suited for other wavelength ranges (e.g. HgCdTe detectors for the mid-infrared). A data acquisition device 52 is in electrical communication with detector 50, for generating a waveform indicative of the time dependence of the signals from detector 50. Device 52 is preferably a scalar; alternatively, device 52 can include an oscilloscope or a boxcar. Data analysis and recording electronics 54 are in electrical communication with device 52 (and implicitly with detector 50), and determine values of various parameters of interest from signals characterizing the interaction of intracavity light with sample 38. Preferably, the parameters of interest include parameters measuring the time-dependence of the intracavity light intensity, and in particular ring-down rates for a spectrum of light wavelengths. Absorption spectra may be used for evaluating known compositions or for trace species detection.

Diagnostic components 70 comprise a beam splitter 72, which sends parts of diagnostic beam 48 to a wavelength-meter 74 and to a scanning confocal interferometer 76. Wavelength meter 74 is connected and sends data to data analysis electronics 54. Other suitable diagnostic elements may include a CCD camera for analyzing the transverse spatial distribution of diagnostic beam 48, for example.

FIG. 2-A is a schematic diagram illustrating cavity 30. An acousto-optic modulator 32 serves as the input of cavity 30. For information on acousto-optic modulators see for example Yariv, *Ouantum Electronics,* John Wiley & Sons, New York, 1989. Briefly, in an AOM a pressure transducer creates a sound wave that modulates the index of refraction in an active nonlinear crystal, through the photoelastic effect. The sound wave produces a Bragg diffraction grating that disperses incoming light into multiple orders. The diffracted light is frequency-shifted by an amount equal to the acoustic wave frequency, as can be illustrated by conservation of energy or Doppler-shift arguments. The pressure transducer of AOM 32 is controlled by an electrical signal 86 received from function generator 85.

If AOM 32 is off it allows beam 47a to pass through undeflected. If AOM 32 is on it deflects part of beam 47a onto an intracavity light path 51 to generate an intracavity light beam 53; some light is absorbed by AOM 32 (~0.1%), while the rest passes through undeflected as a zeroth order beam 47c. Zeroth order beam 47c does not follow intracavity light path 51. AOM 32 is preferably situated at a Brewster's angle relative to beam 47a, such that intracavity beam 53 is linearly polarized even if beam 47a is unpolarized. AOM 32 is preferably antireflection coated for the wavelength of interest, in order to minimize losses within cavity 30. The reflection 47d of input beam 47a from AOM 32 is not directed back toward light source 40, leading to a reduction in optical feedback to light source 40.

Intracavity light path 51 is defined between high-reflectivity mirrors 33a, 33b, and a moderate-reflectivity (>95%, but less than 100%) mirror 34 serving as the output of cavity 30. Mirrors 33a–b and 34 are situated such that cavity 30 is a high-finesse optical resonator (Fabry-Perot cavity). Cavity 30 has a physical length on the order of meters to tens of meters, and an intracavity pathlength two to five orders of magnitude higher than its physical length. Physical lengths on the order of tens of meters can be achieved using a folded cavity structure as a modified White cell, as is well known in the art. A sample 38 is situated within light path 51. Sample 38 is preferably a gas situated within the entirety of intracavity light path 51, but in general may be solid or liquid, and may be situated anywhere within light path 51. Cavity 30 is a passive cavity, i.e. is not a laser cavity with gain.

Figure 3:
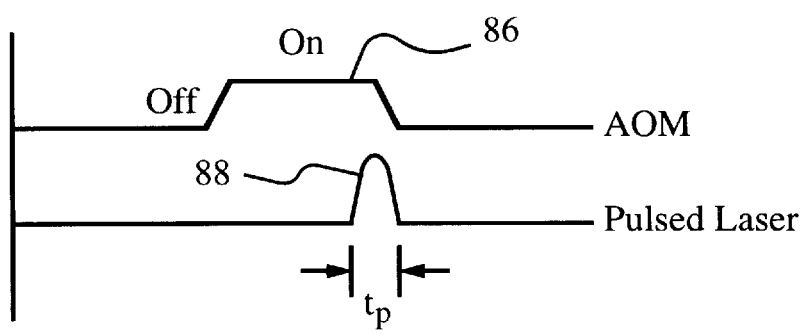
FIG. 3 illustrates preferred relative timings of input deflector and laser pulses for a system comprising a pulsed laser, according to the present invention.

FIG. 3 shows preferred relative timings of the on-periods of AOM 32 and light source 44. AOM 32 is on (represented by pulse 86) as a pulse 88 generated by light source 40 is incident on AOM 32. Pulse 88 has a duration $t_p$ which is shorter than the time it takes the start of pulse 88 to reach AOM 32 following reflections by mirrors 33b and 34. In order to maximize the amount of light coupled into cavity 30, AOM 32 is preferably turned off before the first reflection of pulse 88 reaches AOM 32, such that AOM 32 does not deflect the first reflection of pulse 88. For laser pulses between 2 and 20 ns in duration and AOM turnoff times of less than 5 ns, cavity lengths higher than 60 cm generally allow turning off the AOM before the incidence of the first reflected pulse.

AOM 32 may also be used to couple a continuous wave into cavity 30. AOM 32 is then continuously on. In such an embodiment, AOM 32 introduces additional losses into cavity 30, as some (but not all) intracavity light extending from mirrors 33a–b and incident on AOM 32 is deflected out of intracavity light path 51 and out of cavity 30. AOM 32 is then turned off, and the decay of intracavity light is measured as described above. In such an embodiment, the turn-off time of AOM 32 is no longer relevant; the overall amount of coupling is simply reduced by a factor (1-AOM diffraction efficiency). For a typical AOM, about 40% of a short pulse is coupled into cavity 30, while 24% is coupled for a long pulse.

The use of a deflection means such as an acousto-optic modulator for coupling light into cavity 30 allows relatively high in-coupling efficiencies, and correspondingly high intracavity light intensities. The use of an acousto-optic modulator allows in-coupling efficiencies of about 40%, which is two to three orders of magnitude higher than the 0.001–0.1% efficiencies achieved with typical input mirrors. A two to three order of magnitude in signal leads to a one to two order of magnitude increase in signal-to-noise ratio, as SNR generally varies with the square root of the signal.

Preferably, the absorption losses introduced by AOM 32 are not substantially higher than the losses introduced by output mirror 34. The frequency shift (typically 50 to 500 MHz) introduced by AOM 32 is preferably taken into account for high-resolution spectroscopy applications. For short (<5 ns), non-Fourier-transform-limited pulses with wide linewidths (>1 GHz) and significant frequency jitter, typical frequency shifts due to AOM 32 may be neglected. The AOM shift does not affect pulse shape, or the exponential time dependence of intracavity light intensity; however, wavelength calibration may be required for high-resolution, high-sensitivity measurements.

An in-coupling scheme using a deflection means is particularly useful for far-infrared spectroscopy applications, for which it is particularly difficult to manufacture mirrors that have high-reflectivity but are not perfectly reflective, and for which photon-counting detectors (e.g. photomultiplier tubes) are not widely available. For far-infrared applications, mirrors 33*a–b* are perfectly reflective, while mirror 34 preferably has a small aperture for allowing some light to exit cavity 30. A mirror similar to mirror 34 would be difficult to use for coupling light into cavity 30.

Figure 4:
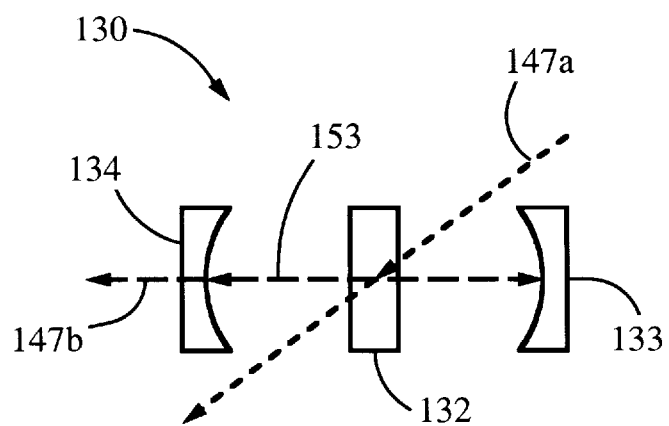
FIG. 4 shows a linear cavity comprising an intracavity input deflector, according to the present invention.

Various cavity geometries may be suitable for use in a system of the present invention. FIG. 4 shows a linear resonant cavity 130 enclosing an input deflector 132. When on, deflector 132 deflects part of an incident beam 147*a* onto a linear intracavity light path 153. Undeflected light is marked 147*c*. The light within cavity 130 (preferably a pulse) rings down between a high-reflectivity mirror 133 and a moderate-reflectivity output mirror 134, producing an exponentially decaying light beam 147*b* (preferably a pulse sequence) exiting output mirror 134.

Intracavity-deflectors such as acousto-optic modulators have been used previously for dumping light outside of active (lasing) cavities. For information on the use of AOMs at Brewster's angle for laser cavity dumping and Q-switching see the articles by Chesler and Maydan in *J. Appl. Phys.* 42:1028–1031 (1971), Chesler and Maydan in *J. Appl. Phys.* 42:1031–1034 (1971), and Chesler et al. in *J. Appl. Phys.* 41:4125–4127 (1970). FIG. 2-B illustrates schematically a prior-art device 10 in which an AOM 11 is situated within a lasing resonant cavity defined by mirrors 12*a–c*. AOM 11 deflects light generated by an active element (laser) 13 from an intracavity light path 14, to generate an output beam 15 which exits the resonant cavity. AOM 11 is placed within the cavity at Brewster's angle, and is antireflection coated. Typical pulse durations are between 10 ns and 100 ns, with repetition rates of kHz to MHz and peak powers 10 to 100 times higher than under normal c.w. operation.

Generally, any device which deflects light onto the intracavity light path while allowing the measurement of exponentially varying intracavity light intensities may be suitable as an input deflection means. Preferably, such as device selectively deflects extracavity light onto the intracavity light path when on, while letting a suitable part (preferably, substantially all) of intracavity light to pass undeflected when off. Such an input deflection means can be an electro-optic modulator. For information on electro-optic modulators see for example Demtröder, *Laser Spectroscopy,* Springer, Berlin, 1996. While electro-optic modulators can have faster switch-off times than acousto-optic modulators, they also introduce relatively high losses that degrade cavity finesse and thus measurement sensitivity. Other potential input deflection means include rotating mirrors, beamsplitters, saturable absorbers, and thin-film absorbers. Rotating mirrors are difficult to implement in practice. Beamsplitters introduce very high losses which may not allow the measurement of exponentially varying intracavity light intensities. Saturable and thin-film absorbers introduce gain in the cavity, which may result in non-exponential, complex output waveforms.

It will be clear to one skilled in the art that the above embodiment may be altered in many ways without departing from the scope of the invention. For example, a system of the present invention is not limited to CRDS applications. Accordingly, the scope of the invention should be determined by the following claims and their legal equivalents.

What is claimed is:

1. An optical system comprising:
   a) a light source;
   b) a resonant cavity in optical communication with said light source, said resonant cavity defining an intracavity light path, a sample being situated within said light path;
   c) an input deflection means situated within said intracavity light path, for deflecting light generated by said light source onto said intracavity light path, wherein said input deflection means is capable of allowing intracavity light along said intracavity light path to pass substantially undeflected; and
   d) a detection means in optical communication with said resonant cavity, for detecting light of a wavelength of interest extending from said cavity, thereby measuring an interaction of intracavity light of said wavelength with said sample.

2. The system of claim 1 wherein said light generated by said light source comprises a light pulse.

3. The system of claim 1 wherein said input deflection means comprises an acousto-optic modulator.

4. The system of claim 1 wherein said input deflection means comprises an electro-optic modulator.

5. The system of claim 1 wherein said detection means comprises a photovoltaic detector.

6. The system of claim 1 wherein said wavelength is in a far-infrared range.

7. The system of claim 1 further comprising a wavelength tuning means for varying said wavelength within a range, for generating an absorption spectrum of said sample for said range.

8. The system of claim 1 wherein said light source is situated such that light extending from said input deflection means is not directed toward said light source.

9. The system of claim 1 wherein said light source is situated such that light generated by said light source is not normal to said input deflection means, such that light reflected by said input deflection means is not directed toward said light source.

10. The system of claim 1 wherein said light source is monochromatic.

11. The system of claim 10 wherein said light source is tunable.

12. The system of claim 1 wherein said light source comprises a laser.

13. The system of claim 12 wherein said laser is a semiconductor laser.

14. The system of claim 12 wherein said light source further comprises an optical isolation means in optical communication with an output of said laser, for reducing an optical feedback to said laser.

15. The system of claim 1 further comprising a data analysis means in communication with said detection means, for receiving a signal characterizing said interaction, and determining from said signal a value of a parameter of interest characterizing a time-dependence of an intensity of said intracavity light.

16. The system of claim 15 wherein said parameter of interest is an exponential rate characterizing said time-dependence.

17. The system of claim 15 wherein said parameter of interest is a ring-down rate.

18. An optical system comprising:
   a) a tunable light source;
   b) a ring-down resonant cavity defining an intracavity light path, for holding a sample within said intracavity light path;
   c) an input deflection means situated within said intracavity light path, for deflecting light generated by said light source onto said intracavity light path while allowing intracavity light to pass substantially undeflected, wherein said intracavity light comprises a wavelength within an absorption region of interest of said sample;
   d) a detection means in optical communication with an output of said cavity, for detecting a time-dependence of an intensity of said intracavity light; and
   e) a data analysis means in electrical communication with said detection means, for determining an exponential rate characterizing said time-dependence, said exponential rate being indicative of an absorption of said sample at said wavelength.

19. An optical system comprising:
   a) a pulsed light source for generating a light pulse;
   b) a ring-down resonant cavity defining an intracavity light path, for holding a sample within said intracavity light path;
   c) an input deflection means situated within said intracavity light path, for deflecting said light pulse onto said intracavity light path while allowing said light pulse to travel substantially undeflected along said intracavity light path;
   d) a detection means in optical communication with an output of said cavity, for detecting a time-dependence of an intensity of said pulse at a wavelength of interest; and
   e) a data analysis means in electrical communication with said detection means, for determining an exponential rate characterizing said time-dependence, said exponential rate being indicative of an absorption of said sample at said wavelength.

20. An optical system comprising:
   a) a tunable light source comprising a laser;
   b) a ring-down resonant cavity defining an intracavity light path, for holding a sample within said intracavity light path;
   c) an acousto-optic modulator situated at Brewster's angle within said intracavity light path, for deflecting light generated by said light source onto said light path to generate a light pulse traveling along said intracavity light path, wherein said acousto-optic modulator allows said light pulse to travel substantially undeflected along said intracavity light path;
   d) a detection means in optical communication with an output of said cavity, for detecting a time-dependence of an intensity of said pulse at a wavelength of interest; and
   e) a data analysis means in electrical communication with said detection means, for determining an exponential rate characterizing said time-dependence, said exponential rate being indicative of an absorption of said sample at said wavelength.

21. A method of performing an optical measurement, comprising the steps of:
   a) generating input light incident on a resonant cavity containing a sample;
   b) deflecting said input light onto an intracavity light path for illuminating said sample with intracavity light comprising a wavelength corresponding to an absorption region of interest of said sample, such that light traveling along said intracavity light path is substantially undeflected; and
   c) detecting an intracavity intensity of light of said wavelength.

22. The method of claim 21 further comprising a step of determining an exponential rate characterizing a time-dependence of said intracavity intensity, for generating an absorption spectrum of said sample.

23. The method of claim 21 further comprising a step of determining a level of a trace species within said sample using said intracavity intensity.

24. A method of performing an optical measurement, comprising the steps of:
   a) generating input light incident on a resonant cavity containing a sample;
   b) turning on an input deflection means for deflecting said input light onto an intracavity light path, for generating an intracavity light pulse illuminating said sample at a wavelength corresponding to an absorption region of interest of said sample;
   c) turning off said input deflection means such that said intracavity light pulse travels along said intracavity light path substantially undeflected by said input deflection means;
   d) detecting a time-dependence of an intracavity intensity of light of said wavelength; and
   e) determining a rate characterizing said time-dependence, for generating an absorption spectrum of said sample.

* * * * *

UNITED STATES PATENT AND TRADEMARK OFFICE
CERTIFICATE OF CORRECTION

PATENT NO.    : 5,815,277
DATED         : September 29, 1998
INVENTOR(S)   : Zare, Richard N. et al.

It is certified that error appears in the above-identified patent and that said Letters Patent is hereby corrected as shown below:

<u>Title page,</u>
Item [73], please correct the Assignee from "The Board of Trustees of the Leland Stanford Junior University" to -- The Board of Trustees of the Leland Stanford Junior University --.

Signed and Sealed this

Twenty-first Day of January, 2003

JAMES E. ROGAN
*Director of the United States Patent and Trademark Office*